United States Patent [19]

Drabek et al.

[11] 4,342,778
[45] Aug. 3, 1982

[54] INSECTICIDAL
(2,3-DIHYDRO-2,2-DIMETHYLBENZOFU-
RAN-7-YLOXY-N-METHYLCARBAMOYL)-
(N'-ALKOXYCARBAMOYL)-SULPHIDES

[75] Inventors: Jozef Drabek, Oberwil, Switzerland;
Manfred Böger, Weil am Rhein, Fed.
Rep. of Germany

[73] Assignee: Ciba-Geigy Corporation, Ardsley, N.Y.

[21] Appl. No.: 35,048

[22] Filed: May 1, 1979

Related U.S. Application Data

[63] Continuation of Ser. No. 958,302, Nov. 6, 1978, abandoned, which is a continuation of Ser. No. 887,271, Mar. 16, 1978, abandoned.

[30] Foreign Application Priority Data

Mar. 25, 1977 [CH]  Switzerland ............... 3808/77
Jan. 31, 1978 [CH]  Switzerland ............... 1039/78

[51] Int. Cl.³ .................. A01N 47/10; C07D 307/86
[52] U.S. Cl. ........................... 424/285; 549/467
[58] Field of Search ............... 260/346.73; 424/285

[56] References Cited

U.S. PATENT DOCUMENTS 3,843,688  10/1974  Cleveland ............... 260/346.73

FOREIGN PATENT DOCUMENTS 848911  5/1977  Belgium.

Primary Examiner—Henry R. Jiles
Assistant Examiner—Bernard Dentz
Attorney, Agent, or Firm—Frederick H. Rabin

[57] ABSTRACT

Compounds of the formula

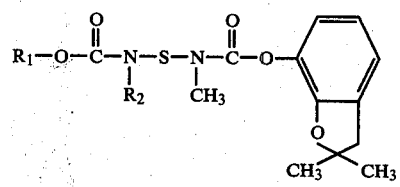

wherein $R_1$ is $C_1$–$C_{10}$-alkyl, $C_1$–$C_2$-alkoxy-$C_1$–$C_2$-alkyl or cyclohexyl and $R_2$ is $C_1$–$C_4$-alkyl possessing valuable insecticidal properties.

3 Claims, No Drawings

INSECTICIDAL (2,3-DIHYDRO-2,2-DIMETHYLBENZOFURAN-7-YLOXY-N-METHYLCARBAMOYL)-(N'-ALKOXYCARBAMOYL)-SULPHIDES

This is a continuation of application Ser. No. 958,302, filed on Nov. 6, 1978, which was a continuation of application Ser. No. 887,271, filed on Mar. 16, 1978, both now abandoned.

The present invention relates to novel, pesticidally active (2,3-dihydro-2,2-dimethylbenzofuran-7-yloxy-N-methylcarbamoyl)-(N'-alkoxycarbamoyl)-sulphides and processes for their production, to pesticidal compositions containing these sulphides as active ingredient and to the use of the novel compounds in controlling pests at a locus.

The (2,3-dihydro-2,2-dimethylbenzofuran-7-yloxy-N-methylcarbamoyl)-(N'-alkoxycarbamoyl)-sulphides of the present invention have the formula I

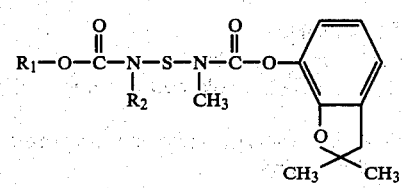

wherein $R_1$ represents a $C_1$-$C_{10}$-alkyl, $C_1$-$C_2$-alkoxy-$C_1$-$C_2$-alkyl or cyclohexyl group and $R_2$ represents a $C_1$-$C_4$-alkyl group.

Alkyl groups in formula I above can be branched or straight chain. Examples of such groups are: methyl, ethyl, n-propyl, isopropyl, n-butyl, sec-butyl, isobutyl and tertbutyl and, for $R_1$, also the n-pentyl, n-hexyl, n-octyl and n-decyl group and the isomers thereof.

Preferred compounds are those of the formula I wherein $R_1$ represents a $C_1$-$C_4$-alkyl group, especially a methyl, propyl or n-butyl group, and most preferably, a n-butyl group.

A further preferred subgroup comprises the compounds of the formula I wherein $R_2$ represents an ethyl, propyl or butyl group, especially a n-butyl group, and, most particularly, those compounds wherein additionally $R_1$ has the above preferred meanings.

Particularly preferred compounds are those of the formula I wherein either $R_1$ or $R_2$ represents a n-butyl group.

The novel compounds of the formula I can be obtained by methods which are in themselves known, for example by (a) reacting a compound of the formula II

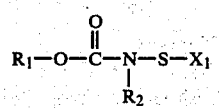

wherein $R_1$ and $R_2$ have the meanings given above and $X_1$ represents a halogen atom, especially a chlorine or bromine atom with a compound of the formula III

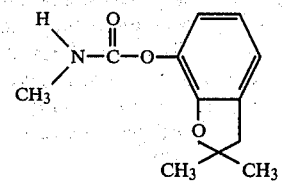

said reaction being carried out in the presence of a base; or (b) reacting a compound of the formula IV

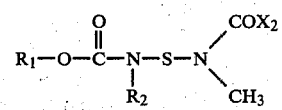

wherein $R_1$ and $R_2$ have the meanings given above and $X_2$ represents a halogen atom, especially a fluorine or chlorine atom with a compound of the formula V

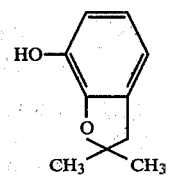

said reaction being carried out in the presence of a base.

Advantageously, process (a) is carried out at a reaction temperature between $-10°$ and $+50°$ C., and process (b) at a temperature between $-10°$ and $+100°$ C. The reactions can be carried out under normal or elevated pressure, optionally in a solvent or diluent which is inert to the reactants, and optionally in the presence of a base.

Suitable solvents or diluents for these reactions are for example ethers and ethereal compounds, such as diisopropyl ethers, dioxane, di-methoxy ethane and tetrahydrofurane; amides, such as N,N-dialkylated carboxy amides; aliphatic, aromatic and halogenated hydrocarbons, especially benzene, toluene, xylenes, chlorobenzene, dichloromethane, chloroform and tetrachloromethane; nitriles, such as acetonitrile; dimethyl sulphoxide; and ketones, such as acetone and methyl ethyl ketone.

Suitable bases are in particular tertiary amines, such as triethylamine, dimethyl aniline, pyridine, picolines and lutidines, as well as hydroxides, oxides, carbonates and bicarbonates of alkali metals and alkaline earth metals; and also alkali metal alcoholates, for example potassium tertbutylate and sodium methylate.

The compounds of the formulae II to V used as starting materials are known or they can be prepared by methods analogous to known ones.

Surprisingly, it has now been found that the compounds of the formula I have a very good broad-spectrum insecticidal action and, accordingly, can be used for controlling a variety of insects, especially for controlling the eggs, larvae, nymphs, pupae and/or adults of insects which are harmful to animals or plants.

In particular, however, the compounds of the present invention have a valuable action against insect pests of the orders Coleoptera and Lepidoptera, for example *Leptinotarsa decemlineata, Anthonomus grandis* and *Dys-*

*dercus fasciatus.* In addition, individual compounds of the formula I have both a good systemic and contact action against aphids, for example of the species *Myzus persicae* and *Aphis fabae*, and against citrus mealy bugs, for example *Pseudococcus citri.* Accordingly, the active compounds of the formula I are especially suitable for controlling pests in crops of vegetables, cotton, fruit and in ornamentals.

The insecticidal action of the compounds of the invention can be substantially broadened and adapted to prevailing circumstances by addition of other pesticides, for example insecticides and acaricides. Examples of suitable additives include: organic phosphorus compounds, nitrophenols and derivatives thereof, formamidines, ureas, pyrethroids, carbamates, and chlorinated hydrocarbons.

The compounds of the formula I may be used as pure active substance or together with suitable carriers and/or additives. Suitable carriers and additives can be solid or liquid and correspond to the substances conventionally used in the art of formulation, for example natural or regenerated substances, solvents, dispersants, wetting agents, tackifiers, thickeners, binders and/or fertilisers.

For application, the compounds of the formula I may be processed to dusts, emulsifiable concentrates, granules, dispersions, sprays, to solutions, or suspensions, in the conventional formulation which is commonly employed in application technology.

The compositions of the present invention are prepared in known manner by homogeneously mixing and/or grinding active substances of the formula I with the suitable carriers, with or without the addition of dispersants or solvents which are inert to the active substances.

The compounds of the formula I may be processed to the following formulations:

Dusts, tracking powders and granules (coated granules, impregnated granules and homogeneous granules).

Liquid formulations:

(a) water-dispersible active substance concentrates: wettable powders, pastes and emulsions;

(b) solutions.

The content of active substance in the above described compositions is between 0.1% and 95%.

The compounds (active substances) of the formula I can, for example, be formulated as follows (throughout the present specification all parts and percentages are by weight):

DUSTS

The following substances are used to manufacture (a) a 5% and (b) a 2% dust:

(a)

5 parts of active substance
95 parts of talc;

(b)

2 parts of active substance,
1 part of highly disperse silicic acid,
97 parts of talc.

The active substances are mixed with the carriers and ground.

GRANULES

The following substances are used to produce 5% granules:

5 parts of active substance,
0.25 parts of epichlorohydrin,
0.25 parts of cetyl polyglycol ether,
3.50 parts of polyethylene glycol,
91 parts of kaolin (particle size 0.3–0.8 mm).

The active substance is mixed with epichlorohydrin and the mixture is dissolved in 6 parts of acetone; the polyethylene glycol and cetyl polyglycol ether are then added. The resultant solution is sprayed on kaolin, and the acetone is subsequently evaporated in vacuo.

WETTABLE POWDERS

The following constituents are used for the preparation of (a) a 40%, (b) and (c) a 25%, and (d) a 10% wettable powder:

(a)

40 parts of active substance,
5 parts of sodium ligninsulphonate,
1 part of sodium dibutylnaphthalenesulphonate,
54 parts of silicic acid.

(b)

25 parts of active substance,
4.5 parts of calcium ligninsulphonate,
1.9 parts of Champagne chalk/hydroxyethyl cellulose mixture (1:1),
1.5 parts of sodium dibutylnaphthalenesulphonate,
19.5 parts of silicic acid,
19.5 parts of Champagne chalk,
28.1 parts of kaolin, (c)

25 parts of active substance,
2.5 parts of isooctylphenoxy-polyoxyethyleneethanol,
1.7 parts of Champagne chalk/hydroxyethyl cellulose mixture (1:1),
8.3 parts of sodium aluminum silicate,
16.5 parts of kieselguhr,
46 parts of kaolin;

(d)

10 parts of active substance,
3 parts of a mixture of the sodium salts of saturated fatty alcohol sulphates,
5 parts of naphthalenesulphonic acid/formaldehyde condensate,
82 parts of kaolin.

The active substances are homogeneously mixed with the additives in suitable mixers and the mixture is then ground in appropriate mills and rollers. Wettable powders are obtained which can be diluted with water to give suspensions of the desired concentration.

EMULSIFIABLE CONCENTRATES

The following substances are used to produce (a) a 10%, (b) a 25% and (c) a 50% emulsifiable concentrate:

(a)

10 parts of active substance,
3.4 parts of epoxidised vegetable oil,
3.4 parts of a combination emulsifier consisting of fatty alcohol polyglycol ether and alkylarylsulphonate calcium salt,
40 parts of dimethyl formamide,
43.2 parts of xylene;

(b)

25 parts of active substance,
2.5 parts of epoxidised vegetable oil,
10 parts of alkylarylsulphonate/fatty alcohol polyglycol ether mixture,
5 parts of dimethyl formamide,
57.5 parts of xylene;

(c)

50 parts of active substance,
4.2 parts of tributylphenol-polyglycol ether,
5.8 parts of calcium dodecylbenzenesulphonate,
20 parts of cyclohexanene,
20 parts of xylene.

By diluting these concentrates with water it is possible to obtain emulsions of the required concentration.

SPRAYS

The following ingredients are used to prepare (a) a 5% spray, and (b) a 95% spray:

(a)

5 parts of active substance,
1 part of epichlorohydrin,
94 parts of ligroin (boiling range 160°–190° C.);

(b)

95 parts of active substance,
5 parts of epichlorohydrin.

The invention is further illustrated by the following Examples.

EXAMPLE 1

Preparation of
(2,3-dihydro-2,2-dimethyl-benzofuran-7-yloxy-N-methylcarbamoyl)-(methoxy-N'-n-butylcarbamoyl)-sulphide To a solution of 8.5 g of methyl-N-n-butylurethane in 70 ml of methylene chloride were slowly added 8.7 g of $SCl_2$ at a temperature of 0° to 5° C. Then 7.1 g of triethylamine were slowly added dropwise to the solution. The reaction mixture was stirred for a further 30 minutes at 0° to 5° C. After distillation of the residue, the crude intermediate was suspended in petroleum ether, collected by filtration, and the solvent was distilled off.

The resulting N-chlorosulphenyl-N-n-butylmethylurethane was added, with constant stirring, at a temperature of 5° to 10° C. to a solution of 14 g of 2,3-dihydro-2,2-dimethyl-benzofuran-7-yl-methylcarbamate in 70 ml of methylene chloride. Then 7 g of pyridine were added dropwise to the reaction mixture at 5° to 10° C. and the resulting solution was stirred for a further 12 hours at room temperature.

The solvent was distilled off and the residue suspended in benzene. The suspension was filtered and the benzene subsequently distilled off, affording the compound of the formula

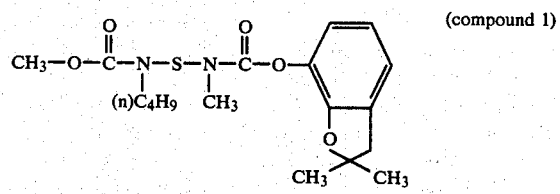

(compound 1)

with a refractive index ($n_D^{20}$) of 1.5289.
The following compounds of the formula I

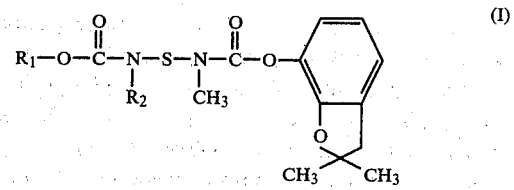

can be obtained in analogous manner:

| Compound | $R_1$ | $R_2$ | Physical data |
|---|---|---|---|
| 2 | $CH_3$ | $CH_3$ | $n_D^{27}$: 1.5273 |
| 3 | $C_2H_5$ | $C_2H_5$ | |
| 4 | (n)$C_4H_9$ | $CH_3$ | $n_D^{20}$: 1.5289 |
| 5 | (n)$C_4H_9$ | (n)$C_4H_9$ | $n_D^{20}$: 1.5248 |
| 6 | (n)$C_{10}H_{21}$ | $CH_3$ | $n_D^{40}$: 1.4868 |
| 7 | $CH_3OCH_2CH_2$ | $CH_3$ | |
| 8 | H | $CH_3$ | $n_D^{45}$: 1.5225 |
| 9 | H | (n)$C_4H_9$ | $n_D^{45}$: 1.5210 |

EXAMPLE 2

Insecticidal action: *Leptinotarsa decemlineata*

Potato plants were sprayed with an aqueous emulsion containing 0.05% of the compound to be tested (obtained from a 10% emulsifiable concentrate).

After the spray coating had dried, the plants were populated with *Leptinotarsa decemlineata* larvae in the L3 stage. Two plants were used for each test compound and insect species. Evaluation of mortality was made after 2, 4, 24 and 48 hours. The test was carried out at 24° C. and 60% relative humidity. In this test, the compounds of Example 1 exhibited a positive stomach poison action against larvae of the species *Leptinotarsa decemlineata*.

EXAMPLE 3

Insecticidal action: *Dysdercus fasciatus*

The test method described in Example 2 was repeated using cotton plants and nymphs of the species *Dysdercus fasciatus* instead of potato plants and *Leptinotarsa decemlineata* larvae.

In this test, the compounds of Example 1 exhibited a good action against larvae of the species *Dysdercus fasciatus*.

EXAMPLE 4

Insecticidal action: (*Anthonomus grandis*)

Cotton plants in pots were sprayed with a spray broth containing 500 ppm of test substance (obtained from a 25% wettable powder) and allowed to dry. Each of the plants was then populated with 5 one-day-old insects of the species *Anthonomus grandis* and the plants were kept in greenhouse compartments at 24° C. and 60% relative humidity.

The number of dead and moribund insects was determined at intervals of 2, 4, 24 and 48 hours respectively after the start of the test. Two plants were used per test substance. In the above test, the compounds of Example 1 exhibited a good action against *Anthonomus grandis*.

EXAMPLE 5

Insecticidal action: *Aphis fabae*

Plants (*Vicia faba*) which have been reared in pots were each populated before the start of the test with approx. 200 aphids of the species *Aphis fabae*. The treated plants were sprayed dripping wet 24 hours later with a solution containing 1000 or 100 ppm of the compound to be tested. Two plants were used for each test compound and test concentration. Evaluation of mortality was made 24 hours later.

In this test, the compounds of Example 1 exhibited a positive action against *Aphis fabae*.

EXAMPLE 6

Insecticidal action: *Myzus persicae*

The test method described in Example 5 was repeated using insects of the species *Myzus persicae* instead of *Aphis fabae*. In this test, compounds of Example 1 exhibited a positive action against *Myzus persicae*.

EXAMPLE 7

Insecticidal action: *Pseudococcus citri*

Plants (*Vicia faba*) which have been reared in pots and cut back to a well-developed pair of leaves, were populated with approx. 200 lice of the species *Pseudococcus citri* 24 hours before the start of the test. The undersides of the leaves populated with lice were then sprayed dripping wet next day with a test solution containing 500 ppm of the compound to be tested. Two plants were used for each test substance and evaluation of mortality was made 24 and 48 hours respectively after the start of the test.

In this test, the compounds of Example 1 acted against *Pseudococcus citri*.

EXAMPLE 8

Systemic action against *Aphis fabae/Myzus persicae*

Bean plants which had grown roots were transplanted into pots containing 600 ccm of soil and then 50 ml of a solution containing 50 ppm or 10 ppm of the compound to be tested (obtained from a 25% wettable powder) were poured directly onto the soil.

After 24 hours the parts of the plants above the soil were populated with aphids of the species *Aphis fabae* or *Myzus persicae* and a plastic cylinder was then slipped over the plants to protect the aphids from any possible contact with the test substance either directly or via the gas phase. The evaluation of mortality was made 48 and 72 hours respectively after the start of the test. Two plants, each in a separate pot, were used per concentration of test substance. The test was carried out at 25° C. and 70% relative humidity.

In this test, compounds of Example 1 exhibited a good systemic action against *Aphis fabae* and *Myzus persicae*.

We claim:

1. The compound of the formula

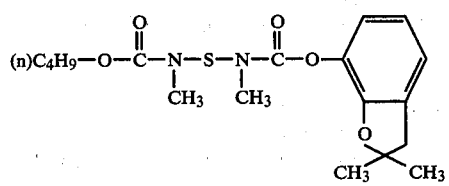

2. An insecticidal composition which comprises an insecticidally effective amount of the compound of claim 1, together with a suitable diluent or carrier therefor.

3. A method of controlling insects at a locus which method comprises applying to said locus an insecticidally effective amount of the compound of claim 1.

* * * * *